US012303393B2

(12) United States Patent
Somani

(10) Patent No.: US 12,303,393 B2
(45) Date of Patent: May 20, 2025

(54) CUSTOM HIP DESIGN AND INSERTABILITY ANALYSIS

(71) Applicant: ICAHN SCHOOL OF MEDICINE AT MOUNT SINAI, New York, NY (US)

(72) Inventor: Sulaiman Somani, New York, NY (US)

(73) Assignee: Icahn School of Medicine At Mount Sinai, New York, NY (US)

( * ) Notice: Subject to any disclaimer, the term of this patent is extended or adjusted under 35 U.S.C. 154(b) by 566 days.

(21) Appl. No.: 17/503,536

(22) Filed: Oct. 18, 2021

(65) Prior Publication Data

US 2022/0039959 A1     Feb. 10, 2022

Related U.S. Application Data

(63) Continuation of application No. PCT/US2020/028499, filed on Apr. 16, 2020.

(60) Provisional application No. 62/834,692, filed on Apr. 16, 2019.

(51) Int. Cl.
| A61F 2/30 | (2006.01) |
| A61F 2/36 | (2006.01) |
| A61F 2/46 | (2006.01) |
| G06F 30/20 | (2020.01) |
| G16H 40/63 | (2018.01) |

(52) U.S. Cl.
CPC .......... *A61F 2/30942* (2013.01); *A61F 2/367* (2013.01); *A61F 2/3676* (2013.01); *A61F 2/4607* (2013.01); *G06F 30/20* (2020.01); *G16H 40/63* (2018.01); *A61F 2002/30738* (2013.01); *A61F 2002/30948* (2013.01); *A61F 2002/30952* (2013.01); *A61F 2002/4633* (2013.01)

(58) Field of Classification Search
CPC ............................ A61F 2/367; A61F 2/30942
See application file for complete search history.

(56) References Cited

U.S. PATENT DOCUMENTS

| 7,517,365 B2 | 4/2009 | Carnigan et al. |
| 10,945,848 B2 | 3/2021 | Unis et al. |
| 11,517,440 B2 | 12/2022 | Unis et al. |

(Continued)

FOREIGN PATENT DOCUMENTS

| EP | 1862151 A1 | 12/2007 |
| EP | 4356854 A2 | 4/2024 |

(Continued)

OTHER PUBLICATIONS

International Search Report and Written Opinion, issued in PCT/US2020/028499 (published as WO 2020/214804), mailed on Jul. 15, 2020, 14 pages.

(Continued)

*Primary Examiner* — Olivia C Chang
(74) *Attorney, Agent, or Firm* — Heslin Rothenberg Farley & Mesiti P.C.

(57) ABSTRACT

Computer implemented methods, systems, and computer products employing program code or algorithms for use in customized patient specific hip implants or femoral stems or sleeves having an outer surface that corresponds more closely to the inner surface of the cortical bone of a patient's femur compared to conventional hip implant or femoral stems or sleeves based on population-based design.

30 Claims, 13 Drawing Sheets

(56) References Cited

U.S. PATENT DOCUMENTS

| | | |
|---|---|---|
| 11,839,548 B2 | 12/2023 | Unis et al. |
| 2007/0118243 A1 | 5/2007 | Schroeder |
| 2008/0009954 A1 | 1/2008 | Mueller et al. |
| 2008/0234833 A1* | 9/2008 | Bandoh ............... A61F 2/30942 623/18.11 |
| 2011/0282473 A1 | 11/2011 | Pavlovskaia et al. |
| 2013/0039592 A1 | 2/2013 | Lang et al. |
| 2013/0197866 A1 | 8/2013 | Wuestemann et al. |
| 2014/0136154 A1 | 5/2014 | Bojarski et al. |
| 2014/0195030 A1 | 7/2014 | Farwell |
| 2014/0263214 A1 | 9/2014 | Dahotre et al. |
| 2015/0030224 A1 | 1/2015 | Mahfouz |
| 2015/0080717 A1 | 3/2015 | Ferko |
| 2015/0119987 A1 | 4/2015 | Davignon et al. |
| 2015/0324114 A1 | 11/2015 | Hurley et al. |
| 2015/0328004 A1 | 11/2015 | Mafhouz |
| 2018/0263782 A1 | 9/2018 | Lang et al. |
| 2019/0060079 A1 | 2/2019 | Unis et al. |
| 2023/0103348 A1 | 4/2023 | Unis et al. |

FOREIGN PATENT DOCUMENTS

| | | | |
|---|---|---|---|
| WO | 2017177182 | A1 | 10/2017 |
| WO | 2020214804 | A1 | 10/2020 |

OTHER PUBLICATIONS

Unis et al., U.S. Appl. No. 17/176,653, entitled "Apparatus, Method and System for Providing Customizable Bone Implants", filed Feb. 16, 2021, 54 pages.

International Search Report and Written Opinion, issued in PCT/US2017/026681 (published as WO 2017/177182), mailed on Sep. 5, 2017, 14 pages.

Extended European Search Report, issued in EP 17779938, dated Nov. 19, 2019, 7 pages.

IP Austrialia, Examination Report No. 1, dated Jun. 21, 2021, 3 pages, Australia.

Extended European Search Report, EP Application No. 20791627.1, 7 pages, Nov. 28, 2022.

International Preliminary Report on Patentability for International Application No. PCT/US2020/028499, Sep. 28, 2021, 13 pages, International Bureau of WIPO.

Somani, Sulaiman, Extended European Search Report for European Application No. 24162496.4 (published as EP4356854), mailed May 23, 2024, 7 pages, May 23, 2024.

\* cited by examiner

CUSTOM HIP DESIGN AND INSERTABILITY ANALYSIS

CROSS REFERENCE TO RELATED APPLICATION

This application is a continuation application International Patent Application No. PCT/US2020/028499, filed on Apr. 16, 2020, entitled "Custom Hip Design And Insertability Analysis" and published under the PCT Articles in English as WO 2020/214804 on Oct. 22, 2020, which International Patent Application perfects and claims the priority benefit of U.S. Provisional Patent Application No. 62/834,692, filed Apr. 16, 2019, entitled "Custom Hip Design and Insertability Analysis," which applications are hereby incorporated herein by reference in their entirety.

FIELD OF THE DISCLOSURE

The present disclosure relates generally to surgical implants for use in total hip arthroplasty or total hip joint replacement, and more particularly to custom patient specific hip implants and methods for forming hip implant components such as femoral stems and femoral sleeves.

BACKGROUND

Currently, hip implants are generally designed through statistical analysis of large datasets involving population-based design. This involves the analysis of comprehensive databases of computed tomography scans (CT-scans), often manually, to design generic geometric implants that are optimized for best fit within the population sample to be characterized by a given implant size or shape. The design process is labor and time sensitive, and the practical execution requires a wide range of scaled geometric shapes to accommodate a range of patient sizes. The process of population selection for a given implant shape and size can be subjective and the acceptable "degree of fit" for specimens within a population sample can likewise be subjective.

Traditional hip implants such as the femoral stems are tapered, thin and symmetrical, and compensate for low bone contact with increased length of the femoral stem. In practice and execution, an analysis of insert ability of a generic implant is not performed for a patient. The implant designer may have simulated implant insertion on members of the population sample during the population-based design process, for example with cadaveric testing, but generally, the insertability and fit of generic implants is determined ex post facto. A surgeon will typically use special rasps to shape and hollow out the femur by cleaning out loose and spongy bone to the shape of the selected standardized femoral stem.

SUMMARY

Shortcomings of the prior art are overcome, and additional advantages are provided through the provision of a computer-implemented method, system and computer product for use in forming a patient specific femoral stem or sleeve of a femoral component for total hip replacement. The method includes, for example: obtaining, by one or more processors, three-dimensional data representing a proximal femur of the patient having centralized cancellous bone and peripheral cortical bone; generating, by the one or more processors, three-dimensional data representing an initial implant having an outer surface corresponding to the inner surface of the peripheral cortical bone of the proximal femur of the patient based on the three-dimensional data representing the proximal portion of the femur of the patient; generating, by the one or more processors, data representing an insertion/removal path through the centralized cancellous bone based on the three-dimensional data representing a proximal portion of the femur of the patient; and generating, by the one or more processors, three-dimensional data representing the patient specific femoral stem or sleeve having a modified outer surface allowing for removal and insertion adjacent to the peripheral cortical bone along the insertion/removal path without obstruction by the inner surface of the cortical bone based on the three-dimensional data representing the proximal portion of the femur of the patient and the data representing the insertion/removal path.

In another embodiment, shortcomings of the prior art are overcome, and additional advantages are provided through the provision of a computer-implemented method, system and computer product for use in forming a patient specific femoral stem or sleeve of a femoral component for total hip replacement. The method includes, for example: obtaining, by one or more processors, three-dimensional data representing a proximal portion of the femur of the patient having centralized cancellous bone and peripheral cortical bone; generating, by the one or more processors, three-dimensional data representing an initial implant having an outer surface corresponding to the inner surface of the peripheral cortical bone of the proximal femur of the patient based on the three-dimensional data representing the proximal femur of the patient; translating, by the one or more processors, the three-dimensional data representing the initial implant from the three-dimensional data representing the proximal portion of the femur of the patient; and generating, by the one or more processors, three-dimensional data representing a patient specific femoral stem or sleeve having a modified outer surface allowing for removal from the peripheral cortical bone along an insertion/removal path without obstruction by the inner surface of the cortical bone based on the translation of the three-dimensional data representing the initial implant and the data representing the proximal portion of the femur of the patient having centralized cancellous bone and peripheral cortical bone.

Additional features are realized through the techniques of the present disclosure. Other embodiments and aspects of the present disclosure are described in detail herein and are considered a part of the claimed disclosure.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

DETAILED DESCRIPTION

Figure 1:
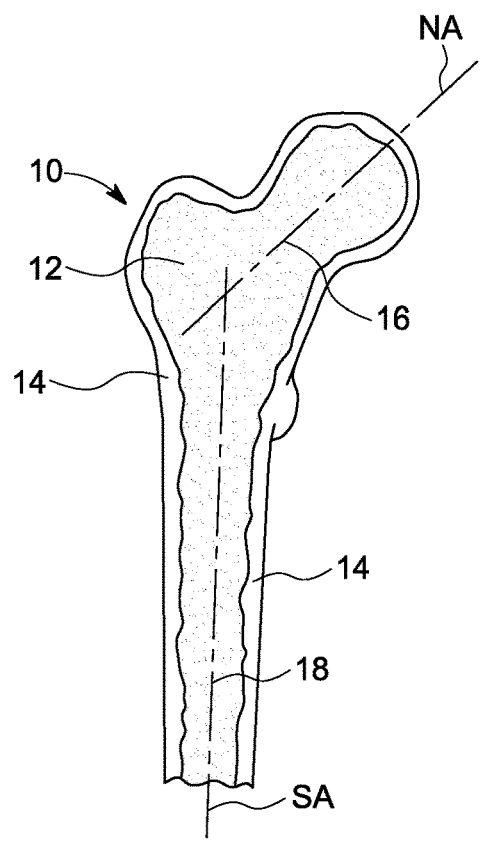
FIGS. 1-4 are cross-sectional views diagrammatically illustrating a computerized process for use in forming a patient specific femoral stem of a femoral component for total hip replacement, according to an embodiment of the present disclosure.

Generally stated, disclosed herein are hip implants, and methods for forming hip implants. For example, the methods may enable providing a tool employing program code or algorithms for use by a surgeon and others in accelerating customized hip implant designs such as femoral stems or femoral sleeves for patient specific total hip arthroplasty or total hip joint replacement.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference.

Positions or directions may be used herein with reference to anatomical structures or surfaces. For example, as the current devices and methods are described herein with reference to use with the bones of the hip, the bones of the hip may be used to describe the surfaces, positions, directions or orientations of the implant apparatus, implant installation apparatus, and surgical methods. Further, the devices and surgical methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and surgical methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the tools and methods, and the aspects, components, features and the like thereof, described herein with respect to a right femur may be mirrored so that they likewise function with a left femur and vice versa.

FIGS. 1-5, FIG. 6, FIG. 13, FIGS. 14-17, and FIG. 22 diagrammatically illustrate computerized processes, for example, implemented, by programming code for use in forming a patient specific femoral stem of a femoral component for total hip replacement, according to embodiments of the present disclosure. FIGS. 7-12, FIG. 13, FIGS. 18-21, and FIG. 22 diagrammatically illustrate computerized processes, for example, implemented, by programming code for use in forming a patient specific femoral sleeve of a femoral component for total hip replacement, according to embodiments of the present disclosure. The patient specific implant may be a femoral sleeve through which a generic stem is fitted and interfaced. The sleeve is designed from preoperative data with an exterior surface that is designed to abut or to be in close proximity with the inner cortical wall of the patient's bone. The sleeve is generally tapered with a wider diameter proximal opening and a smaller diameter distal opening. The generic member is designed to lock into the patient specific member. Given the high forces implants are subjected to and manufacturing efficiencies with generic implants, it may be advantageous in combining a generic implant that is subjected to the predominant biomechanical loads with a patient specific femoral sleeve with optimized stability with the bone.

As will be appreciated from the following description, the present disclosure addresses a challenge for designers of orthopedic hip implants such as femoral stems or femoral sleeves by maximizing implant stability in the cortical bone of the implant while maintaining insertability in a bone preserving way, e.g., volumetrically optimized to minimize size of the femoral stem.

The techniques of the present disclosure may desirably ensure that the implant or femoral stem or sleeve contacts as much cortical bone surface area as possible and that the implant cavity matches the implant shape or femoral stem or sleeve as closely as possible to a specific patient. Stability may be maximized by achieving cortical bone contact along a plurality of implant surface features. An implant or femoral stem or sleeve is generally considered insertable if it can be implanted next to a surgically prepared cavity without fracture or excessive interface micromotion. Maximizing cortical bone contact and maintaining insertability are generally conflicting requirements in the generation of an implant shape or femoral stem or sleeve shape of the hip implant.

In order for a custom hip implant to be stable, the engagement surface needs to make sufficient cortical bone contact to achieve stability. Cortical bone is the dense outer portion of bone that forms a protective layer around the internal cavity. The femoral stem or sleeve needs to be of sufficient length and size to engage the cortical bone. As such, sufficient stability requires implants to be larger, which make them more difficult to insert. Cortical bone is irregular and not symmetrical. The techniques of the present disclosure address achieving high cortical bone surface area contact of implants or femoral stems or sleeves by matching these geometric irregularities. The present disclosure provides tools, methods, and/or systems that may optimize stability and insertability through automated geometric shaping and insertability analysis. Benefits of such an approach include reducing development time and cost while facilitating more personalized and/or customized implant femoral stem or sleeve designs likely to achieve clinical success. Such tools, methods, and/or systems of the present disclosure may facilitate the development of implants or femoral stems or sleeves that are thick and asymmetrical to achieve higher degrees of cortical contact and insertable without extending too far down the shaft of the femur.

The techniques of the present disclosure may include tools, methods, and systems that optimize stability and insertability of hip implants or femoral stems or sleeves by, for example, maximizing initial stability. A determinant of implant viability includes initial stability. For example, the present techniques may be incorporated into design algorithms or program code to accelerate the design of viable implants by auto-solving the challenges of hip implant design, e.g., optimized initial stability and insertability. As another example, the algorithms or program code can be used intra-operatively to visualize an optimized insertion path. Furthermore, the output from the algorithms or program code can be used as inputs to a surgical robot.

Several direct and indirect problems may be solved by the techniques of the present disclosure. For example, conventional implant or femoral stem design is time and resource intensive with viability often only derived intra-operatively. For example, conventional implant or femoral stem insertability is often determined during the surgical procedure by manually testing if the implant can be inserted after the canal has been broached and reamed. When extending the implant or femoral stem design process to high conforming amorphous shapes, the challenges of design are exacerbated.

Furthermore, conventional implants or femoral stems have to be generalized to shapes that are required to work over a wide range of anatomies. Making sure they will work over a diverse range of sizes and shapes is challenging. For example, designing insertable larger circumference implants for conformity with irregular shaped cortical surfaces is not easy due to the constraints of the cavity. In addition, as a result of using generalized shapes, a large range of sizes are required to accommodate anatomical variation. The result is a significant inventory requirement for distributors to carry a wide range of sizes. The present disclosure empowers implant or femoral stem or sleeve designers with tools, methods, and systems to support computerized implant or femoral stem and sleeve design and the development process. The present technique employs data representing the specific configuration of a patient's femur to generate a patient specific femoral stem or sleeve, and is a significant advancement over existing conventional femoral stems or sleeves generated based on data representing data over a large number of patients, none of which data correspond to specific data of a subsequent patient.

For example, an approach for solving the problem of stability and insertability of the femoral stem or sleeve component in a total hip replacement is through a computer implemented method utilizing programming code that may include generating and optimizing an insertion path that may serve as an input to the computerized implant design process. FIGS. 1-5 diagrammatically illustrate a computerized process, for example, implemented, by programming code for use in forming a patient specific femoral stem 100 (FIG. 4) of a femoral component for total hip replacement, according to an embodiment of the present disclosure. For example, FIG. 1 illustrates a proximal portion of a patient's femur 10 having centralized cancellous bone 12 and peripheral cortical bone 14. For example, data representing the patient's proximal femur 10 may include three-dimensional data obtained by, for example, a Computed Tomography (CT) scan, a Computerized Axial Tomography (CAT) scan, a Magnetic Resonance Imaging (MRI) scan, or other suitable two-dimensional imaging or three-dimensional imaging or processing. A femoral shaft axis SA, and a femoral neck axis NA may be operably obtained, derived, or generated from the three-dimensional data of the proximal portion of the patient's femur. A surgeon may input a proximal extreme location 16 and a distal extreme location 18 of the desired patient customized femoral stem implant for femur 10. The proximal extreme location 16 and the distal extreme location 18 may also be auto-generated or auto-determined, for example, based on the data representing the proximal portion of the patient's femur 10 and/or based on predetermined data regarding implant stability. In some embodiments, the distal extreme location 18 may be about 0.5 centimeters (cms) to about 2 cms, about 1 cm to about 1.5 cms, about 0.5 cms, about 1.0 cm, about 1.5 cms, about 2 cms, or other suitable distance below the lesser trochanter 13 of the femur 10. In further embodiments, the distal extreme location 18 may be about 2 cms to about 3 cms, about 2 cms to about 2.5 cms, 2.5 cms to about 3 cms, about 2.5 cms, about 3.0 cms, or other suitable distance below the lesser trochanter 13 of the femur 10.

Figure 2:
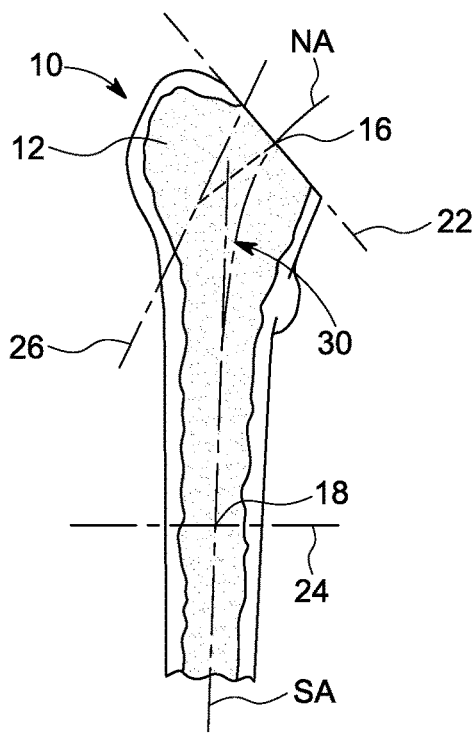

In this approach, as shown in FIG. 2, an insertion/removal path 30 is derived or auto-generated by identifying the proximal extreme location 16 and the distal extreme location 18 of a desired patient customized femoral stem implant for femur 10. For example, a neck plane 22 having an orientation may be generated along femoral neck axis NA and a stem plane 24 having an orientation may be generated along femoral shaft axis SA. Neck plane 22 may be perpendicular to femoral neck axis NA, and stem plane 24 may be perpendicular to femoral shaft axis SA. A further boundary or plane 26 may be generated and orientated through the centralized cancellous bone 12 to define a portion of a boundary for forming the patient specific femoral stem. In other embodiments, a plane may be used that lies in a sagittal plane of the patient and may be used to set a lateral boundary for the initial surface generated at proximal extreme location 16. Alternatively, a surgeon may input planes 22, 24, and 26, and the orientations thereof.

Insertion/removal path 30 may be generated by joining the proximal extreme location 16 and the distal extreme location 18, or joining the intersection of the femoral neck axis NA at the plane 22 and the intersection of the femoral shaft axis SA and the plane 24, for example, by a mathematical approximation to derive a trajectory between the neck plane 22 and stem plane 24. This may be by way of, a nonlimiting example, a curve, a spline, a polynomial, an exponential or a logarithmic function. The governing insertion/removal path 30 describes any continuous curve in arbitrary dimensions represented by a variety of equations that seek to impose or represent certain constraints or properties. By way of a nonlimiting example, different order (linear, quadratic, cubic, etc.), curvature, torsion, basis functions may be used to generate them, or spacing between points (e.g. controlling knot vectors) may be used to define these equations. The insertion/removal path 30 may be aligned with the femoral neck axis NA at the plane 22, and may be aligned with the femoral shaft axis SA at the plane 24. In some embodiments, a resection plane, such as neck plane 22 may be provided, e.g., by input by a surgeon, or based on or utilizing predetermined data. For example, the resection plane or neck plane 22 may be determined as disclosed in U.S. patent application Ser. No. 16/153,334, entitled, "Apparatus, Method and System for Providing Customizable Bone Implants", the entire subject matter of which is incorporated herein by reference.

For example, insertion/removal path 30 may be represented in the 3-coordinate space of the implant and preferably constrained to lie in a single but fully arbitrary plane, e.g. demonstrate 0 torsion. In some embodiments, the insertion/removal path 30 may be disposed along the center of the femur and/or along a coronal plane. For example, the resulting femoral stem 100 (FIG. 4) may be desirably inserted and removed without torsion or rotation along the insertion/removal path 30. In other words, it may be desirable if all of the points on the insertion/removal path 30 lie on a flat plane. By way of a nonlimiting example, this can be achieved by modifying the native femoral neck axis NA and femoral shaft axis SA to lie on a plane defined by a vector connecting the two anchor points and a vector representing the medial-lateral axis of the patient's femur.

Figure 3:
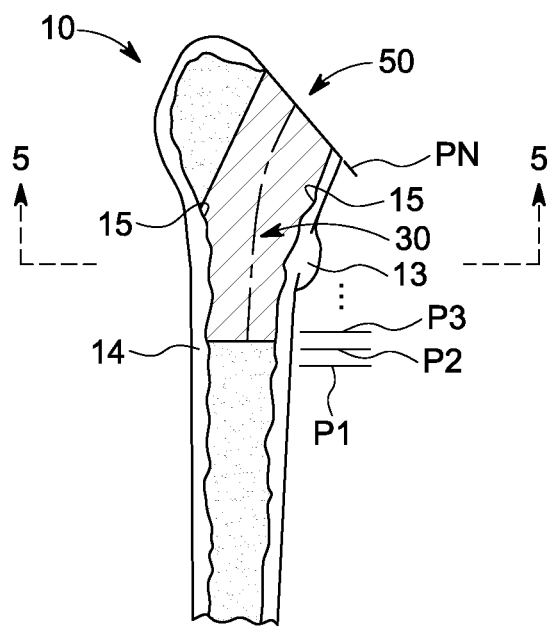

With reference to FIG. 3, once the governing insertion/removal path 30 that represents the trajectory of insertion and removal has been established, an initial implant 50 is constructed or generated. The initial implant 50 is generated element-wise along the insertion trajectory or insertion/removal path 30 to achieve maximal apposition to an inner surface 15 of the cortical bone 14 of the femur 10, along boundary or plane 24 (FIG. 2), and along boundary or plane 26 (FIG. 2).

Figure 4:
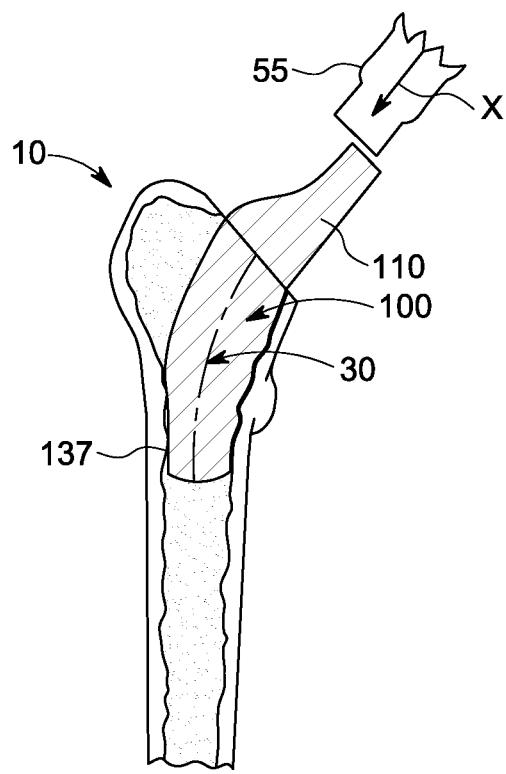
Figure 5:
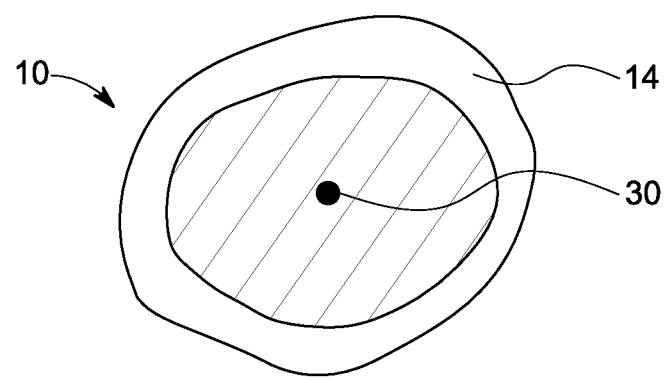
FIG. 5 is an enlarged cross-sectional view taken along line 5-5 in FIG. 3, according to an embodiment of the present disclosure.

By way of a nonlimiting example, as shown in FIG. 5, data representing the governing insertion/removal path 30 may be observable in cross-sectional views of the initial implant 50 at discretized planes, e.g., at planes P1, P2, P3, . . . PN, as shown in FIG. 3, located along the governing insertion/removal path 30 with normal vectors along the insertion/removal path 30 at that point. All planes may lie within all cross-sections of the initial implant along more proximally (towards the neck) located planes along the insertion/removal path 30 of similar definition and similar rotation. For example, all planes P1, P2, . . . Pi, . . . PN, the cross-section at each plane i is ensured to lie within the cross-section of all planes above it (e.g. P(i+1), P(i+2), . . . P(N)). Distal members or cross-sectional portions may be made to "fit" within proximal members or cross-sectional portions with the constraints of definition and fit, to produce a modified initial implant 55, as shown in FIG. 4 that tends to be distally tapered.

Once the modified initial implant 55 is generated, the insertability is tested iteratively. For example, the modified initial implant 55 is removed from the femur, and insertion or translation of the modified implant 55 in the direction of arrow X, as shown in FIG. 4, is simulated along the governing insertion/removal path 30. The program code identifies all of the points causing interferences from each recursive step and removes them from the modified initial implant 55 such that insertability may be achieved, resulting in the patient specific femoral stem 100 as shown in FIG. 4. A neck component 110 may be generated and attachable to or be integral with the patient specific femoral stem 100. In some embodiments, the resultant patient specific femoral stem 100 includes asymmetric cross-sections. In some embodiments, portions, such as portion 137, of the outer surface or outer surface of the resultant patient specific femoral stem 100 may match the corresponding contour and shape of the patient's inner cortical bone surface of the femur.

Figure 6:
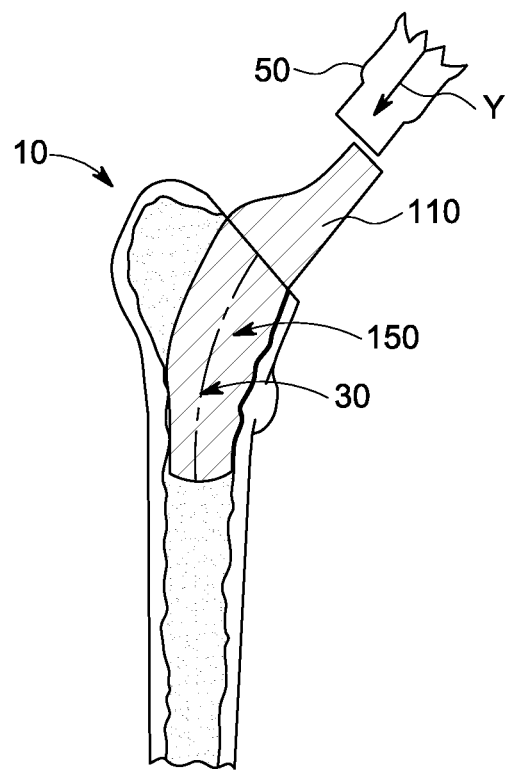
FIG. 6 is a cross-sectional view similar to FIG. 4 diagrammatically illustrating an alternative step in a computerized process for use in forming a patient specific femoral stem of a femoral component for total hip replacement, according to an embodiment of the present disclosure.

In some embodiments, with reference again to FIG. 3, the initial implant 50 may be generated. Once the initial implant 50 is generated, the insertability may be tested iteratively. For example, as shown in FIG. 6, initial implant 50 may be removed from the femur 10, and insertion or translation of the initial implant 50 may be simulated along the governing insertion/removal path 30 in the direction of the arrow Y along the insertion/removal path 30 into femur 10. The program code may identify all of the points causing interferences as the distal end of the initial implant 50 is inserted next to the proximal end of the femur 10. The program code removes portions of the initial implant 50 from the initial implant 50 such that insertability may be achieved, resulting in a patient specific femoral stem 150 as shown in FIG. 6.

It will be appreciated that the governing insertion/removal path 30 may be used to reduce the number of computational steps required to generate the implant compared to the approach described below (e.g., regarding FIGS. 14-17 and FIG. 22), which do not employ an initial insertion/removal path. By way of a nonlimiting example, along the length of the insertion/removal path 30, increasing constraints on the maximum distance of any point on the implant cross-section from the center of the respective insertion/removal path 30 (e.g. "tapering") can be imposed to improve the viability of the implant's insertability.

FIGS. 7-12 diagrammatically illustrate a computerized process, for example, implemented, by programming code for use in forming a patient specific femoral sleeve 400 (FIGS. 10 and 11) of a femoral component for total hip replacement, according to an embodiment of the present disclosure.

Figure 7:
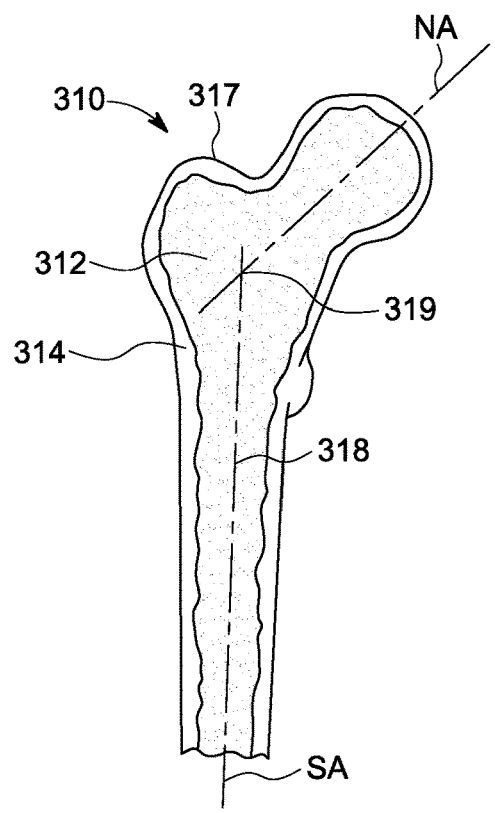
FIGS. 7-10 are cross-sectional views diagrammatically illustrating a computerized process for use in forming a patient specific femoral sleeve of a femoral component for total hip replacement, according to an embodiment of the present disclosure.

For example, FIG. 7 illustrates a proximal portion of a patient's femur 310 having centralized cancellous bone 312 and peripheral cortical bone 314. For example, data representing the patient's proximal femur 310 may include three-dimensional data obtained by, for example, a Computed Tomography (CT) scan, a Computerized Axial Tomography (CAT) scan, a Magnetic Resonance Imaging (MRI) scan, or other suitable two-dimensional imaging or three-dimensional imaging or processing. A femoral shaft axis SA, and a femoral neck axis NA may be operably obtained, derived, or generated from the three-dimensional data of the proximal portion of the patient's femur. A surgeon may input a proximal extreme location 317, a mid-location 319, and a distal extreme location 318 of the desired patient customized femoral sleeve implant for femur 310. The proximal extreme location 317, the mid location 319, and the distal extreme location 318 may also be auto-generated or auto-determined, for example, based on the data representing the proximal portion of the patient's femur 310 and/or based on predetermined data regarding implant stability. The mid location 319 and the distal extreme location 318 may be disposed on the femoral shaft axis SA. The extreme proximal extreme location 317 may be offset from the femoral shaft axis and disposed on an outer surface of the cortical bone 314. The mid location may be disposed on the femoral neck axis NA. In some embodiments, the distal extreme location 318 may be about 0.5 centimeters (cms) to about 2 cms, about 1 cm to about 1.5 cms, about 0.5 cms, about 1.0 cm, about 1.5 cms, about 2 cms, or other suitable distance below the lesser trochanter 13 of the femur 10. In further embodiments, the distal extreme location 18 may be about 2 cms to about 3 cms, about 2 cms to about 2.5 cms, 2.5 cms to about 3 cms, about 2.5 cms, about 3.0 cms, or other suitable distance below the lesser trochanter 13 of the femur 10.

Figure 8:
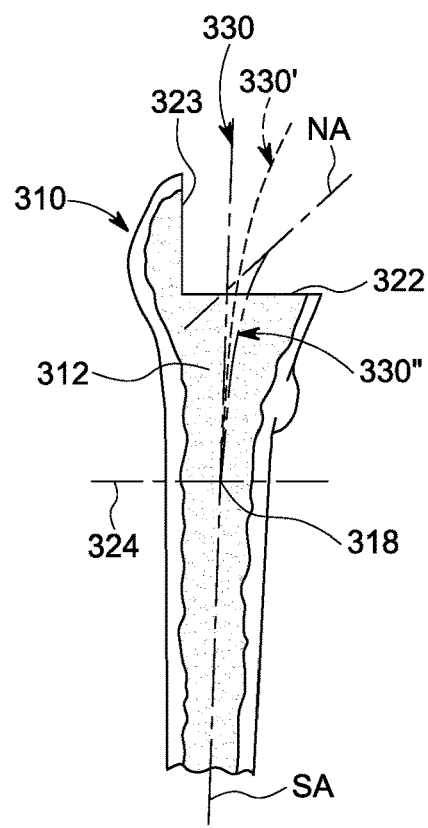

In this approach, as shown in FIG. 8, resection planes, such as a first resection plane 322 and a second resection plane 323 may be provided, e.g., by input by a surgeon, or based on or utilizing predetermined data. For example, the first resection plane 322 may be disposed at 90 degrees from the second resection plane 323. The first resection plane may extend through the proximal extreme location 317 (FIG. 7) and the second resection plane may extend through the mid location 319 (FIG. 7).

Insertion/removal paths may be derived or auto-generated based on the femoral neck axis NA and the femoral shaft axis SA, or solely, the femoral shaft axis SA, and passing through the first plane 322 for use in forming a desired patient customized femoral sleeve. In this illustrated embodiment, a plurality of insertion/removal paths may be generated and later used for selecting an optimized femoral sleeve as described below. For example, a first insertion/removal path 300 may extend superiorly from the distal extreme location 318 and concentric with femoral shaft axis SA. A second insertion/removal path 300' (shown in as a dashed line in FIG. 8) may extend superiorly from the distal extreme location 318 and medially away from femoral shaft axis SA towards first plane 322. A third insertion/removal path 300" may extend superiorly from the distal extreme location 318 and medially away from the femoral shaft axis SA towards plane 322 and then concentric with the femoral neck axis 322. For example, the third insertion/removal path 300" may be a smooth trajectory connecting the femoral shaft axis SA and the femoral neck axis NA. The generation of the plurality of insertion/removal paths may be by a mathematical approximation to derive the trajectories by way of, nonlimiting examples, a straight line, a curve, a spline, a polynomial, an exponential or a logarithmic function. The governing insertion/removal paths describes any continuous straight line or curve in arbitrary dimensions represented by a variety of equations that seek to impose or represent certain constraints or properties. By way of a nonlimiting example, different order (linear, quadratic, cubic, etc.), curvature, torsion, basis functions may be used to generate them, or spacing between points (e.g. controlling knot vectors) may be used to define these equations.

For example, the insertion/removal paths may be represented in the 3-coordinate space of the implant and preferably constrained to lie in a single but fully arbitrary plane, e.g. demonstrate 0 torsion. In some embodiments, the insertion/removal paths may be disposed along the center of the femur and/or along a coronal plane. For example, the resulting femoral sleeve 400 (FIG. 10) may be desirably inserted and removed without torsion or rotation along an optimized insertion/removal path. In other words, it may be desirable if all of the points on the insertion/removal path lie on a flat plane. By way of a nonlimiting example, this can be achieved by modifying the native femoral neck axis NA and femoral shaft axis SA to lie on a plane defined by a vector connecting the two anchor points and a vector representing the medial-lateral axis of the patient's femur.

Figure 9:
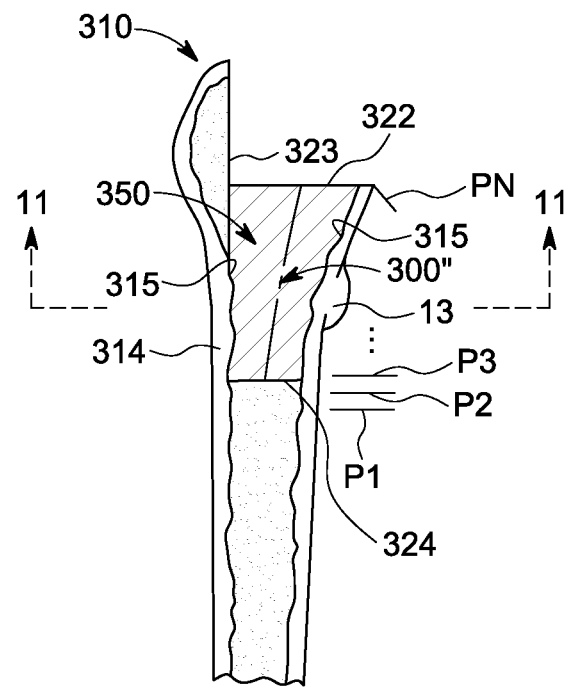

With reference to FIG. 9, selecting one of the insertion/removal paths, e.g., insertion/removal path 300" as shown in FIG. 9, that represents the trajectory of insertion and removal, an initial implant 350 may be constructed or generated. The initial implant 350 may be generated element-wise along the insertion trajectory or insertion/removal path 300" to achieve maximal apposition to an inner surface 315 of the cortical bone 314 of the femur 310, and along planes 322 and 324.

Figure 10:
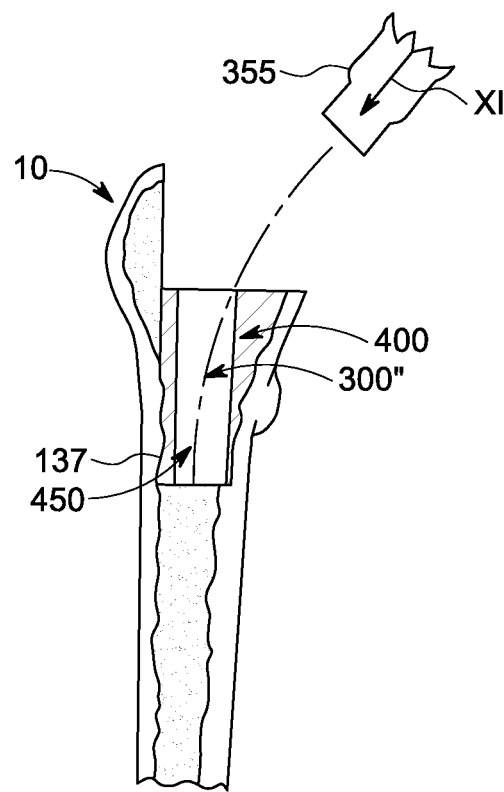
Figure 11:
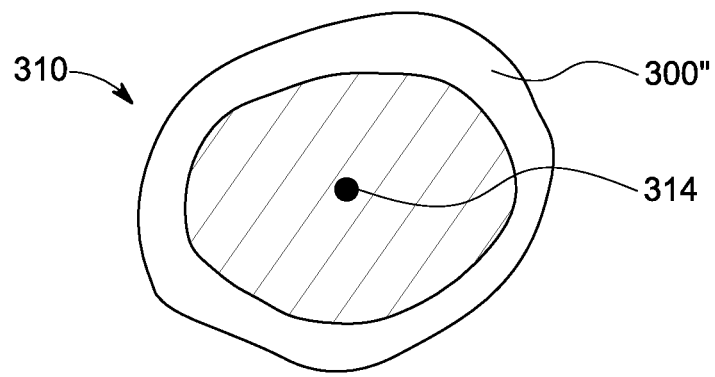
FIG. 11 is an enlarged cross-sectional view taken along line 11-11 in FIG. 9, according to an embodiment of the present disclosure.

By way of a nonlimiting example, as shown in FIG. 11, data representing the governing insertion/removal path 300" may be observable in cross-sectional views of the initial implant 350 at discretized planes, e.g., at planes P1, P2, P3, PN, as shown in FIG. 9, located along the governing insertion/removal path 300" with normal vectors along the insertion/removal path 300" at that point. All planes may lie within all cross-sections of the initial implant along more proximally (towards the neck) located planes along the insertion/removal path 300" of similar definition and similar rotation. For example, all planes P1, P2, . . . Pi, . . . PN, the cross-section at each plane i is ensured to lie within the cross-section of all planes above it (e.g. P(i+1), P(i+2),P(N)). Distal members or cross-sectional portions may be made to "fit" within proximal members or cross-sectional portions with the constraints of definition and fit, to produce a modified initial implant 355, as shown in FIG. 10 that tends to be distally tapered.

Figure 12:
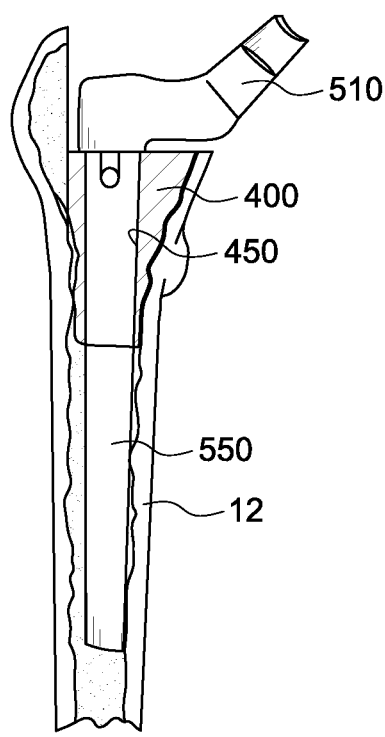
FIG. 12 is an elevational view, in part cross-section, of a patient specific femoral sleeve, and a standard femoral stem and neck, according to an embodiment of the present disclosure.

Once the modified initial implant 355 is generated, the insertability is tested iteratively. For example, the modified initial implant 355 is removed from the femur, and insertion or translation of the modified implant 355 in the direction of arrow X1, as shown in FIG. 10, is simulated along the governing insertion/removal path 300". The program code identifies all of the points causing interferences from each recursive step and removes them from the modified initial implant 355 such that insertability is maintained, resulting in the patient specific femoral sleeve 400 as shown in FIG. 10. The computer implemented method utilizing programming code that may be operable to provide the patient specific femoral sleeve implant 400 with a passageway 450 that may be positionable, aligned, or concentric with the shaft axis SA (FIG. 8). For example, as shown in FIG. 12, the passageway 450 in the patient specific femoral sleeve implant 400 may be sized, located, and orientated relative to the femoral sleeve implant and the patient's femur for receiving a standard or customized femoral stem 550 attached to a neck component 510.

In some embodiments, with reference again to FIG. 9, the initial implant 350 may be generated. Once the initial implant 350 is generated, the insertability may be tested iteratively. For example, the initial implant 350 may be removed from the femur 10, and insertion or translation of the initial implant 350 may be simulated along the governing insertion/removal path 300" in the direction toward the resected femur (in a similar manner as shown in FIG. 6) along the insertion/removal path 300" into the femur 10. The program code may identify all of the points causing interferences as the distal end of the initial implant is inserted next to the proximal end of the femur 10. The program code removes portions of the initial implant from the initial implant such that insertability is guaranteed, resulting in a patient specific femoral sleeve.

It will be appreciated that the governing insertion/removal path 300" may be used to reduce the number of computational steps required to generate the implant compared to the approach described below (e.g., regarding FIGS. 18-21 and FIG. 22), which do not employ an initial insertion/removal path. By way of a nonlimiting example, along the length of the insertion/removal path 300", increasing constraints on the maximum distance of any point on the implant cross-section from the center of the respective insertion/removal path 300" (e.g. "tapering") can be imposed to improve the viability of the implant's insertability.

Such a technique may be extended to any class of shapes whose insertion trajectory into a cavity that is represented by the exact complement of that shape is represented by an insertion/removal path that meets the aforementioned requirements. By way of a nonlimiting example, this includes patient-specific shapes in the orthopedic context, involving tibial and femoral components of total and partial knee implants, acetabular cups for total hip replacements, and the humeral and glenoid components in total shoulder arthroplasty.

Figure 13:
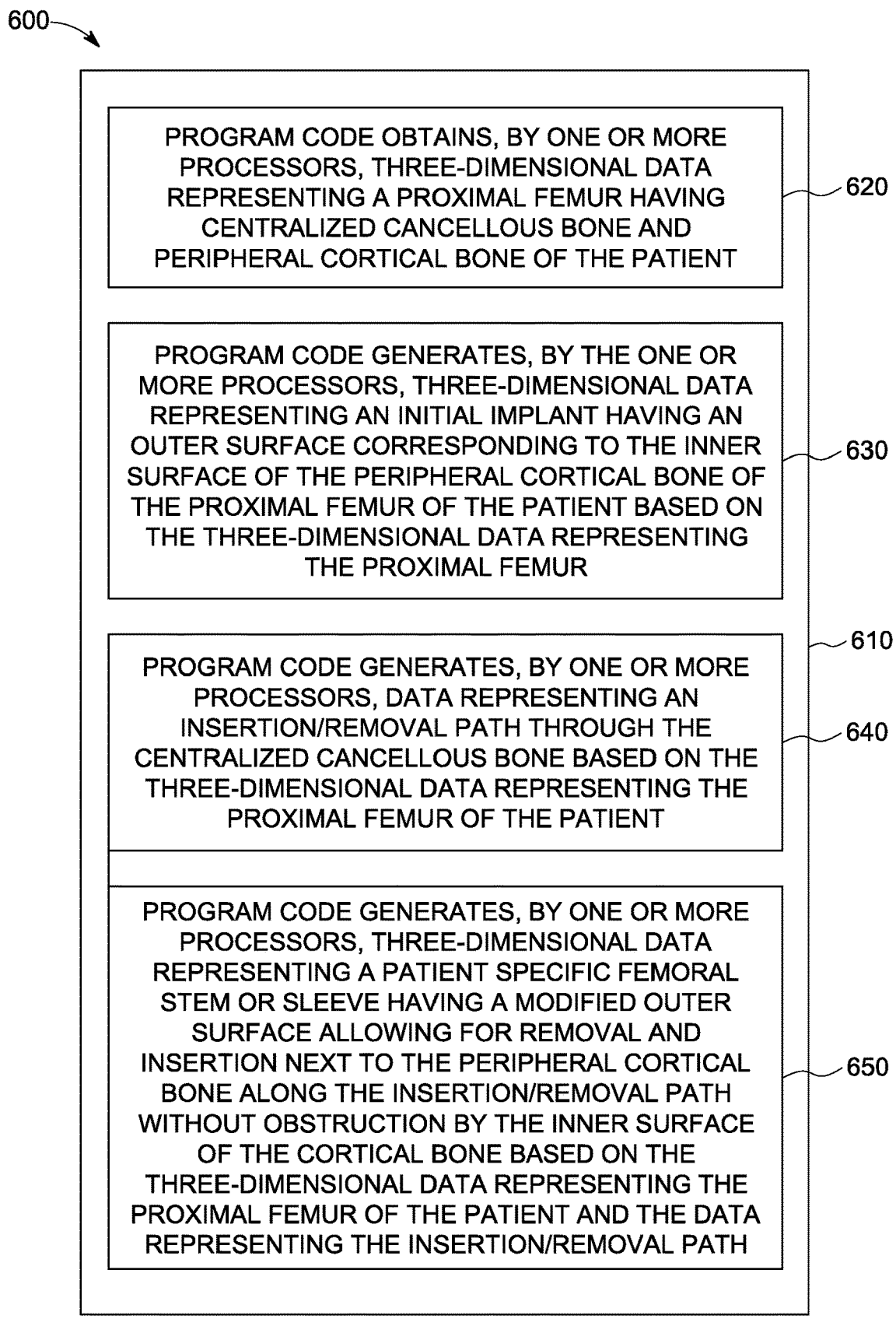
FIG. 13 is a workflow that depicts certain aspects of some embodiments of the present disclosure.

FIG. 13 illustrates a workflow 600 that depicts certain aspects of some embodiments of the present disclosure for use in forming a patient specific femoral stem of a femoral component for a total hip replacement. In some embodiments of the present disclosure, a program code 610 (also referred to as one or more programs) executed by a processing circuit or hardware, obtains at 620, by one or more processors, three-dimensional data representing a proximal femur of the patient having centralized cancellous bone and peripheral cortical bone. At 630, three-dimensional data representing an initial implant having an outer surface corresponding to the inner surface of the peripheral cortical bone of the proximal femur of the patient is generated, by the one or more processors, based on the three-dimensional data representing the proximal femur. At 640, data representing an insertion/removal path through the centralized cancellous bone is generated, by the one or more processors, based on the three-dimensional data representing the proximal femur of the patient. At 650, three-dimensional data representing a patient specific femoral stem or sleeve having a modified outer surface allowing for removal and insertion next to the peripheral cortical bone along the insertion/removal path without obstruction by the inner surface of the cortical bone is generated, by the one or more processors, based on the three-dimensional data representing the proximal femur of the patient and the data representing the insertion/removal path.

In some embodiments, of the present disclosure, a program code executed by a processing circuit or hardware, may obtain, by one or more processors, three-dimensional data representing centralized cancellous bone of a proximal femur of the patient or peripheral cortical bone of a proximal femur of the patient. The three-dimensional data representing an initial implant having an outer surface corresponding to the inner surface of the peripheral cortical bone of the proximal femur of the patient or of the outer surface of the cancellous bone is generated, by the one or more processors, based on the three-dimensional data representing the proximal femur. Data representing an insertion/removal path through the centralized cancellous bone or within the cortical bone is generated, by the one or more processors, based on the three-dimensional data representing the proximal femur of the patient. Three-dimensional data representing a patient specific femoral stem or sleeve having a modified outer surface allowing for removal and insertion next to the peripheral cortical bone along the insertion/removal path without obstruction by the inner surface of the cortical bone is generated, by the one or more processors, based on the three-dimensional data representing the proximal femur of the patient and the data representing the insertion/removal path.

In some embodiments of the present disclosure, the workflow 600 may further include program code for fabricating, by the one or more processors, the femoral stem or femoral sleeve based on the three-dimensional data representing the patient specific femoral stem for the femoral stem. The fabricating of the femoral stem or femoral sleeve may include three-dimensional printing, additive manufacturing forging, or casting based on the data.

In some embodiments of the present disclosure, the generating at 650, the three-dimensional data representing the patient specific femoral stem or femoral sleeve may include program code for translating, by the one or more processors, the three-dimensional data representing the initial implant based on the data representing the insertion/removal path and the three-dimensional data representing a proximal femur of the patient, and program code for modifying, by the one or more processors, the three-dimensional data representing the initial implant based on the translating the three-dimensional data representing the initial implant through the three-dimensional data representing the proximal femur of the patient. The translating may include program code for translating, by the one or more processors, the three-dimensional data representing the initial implant without rotation along the insertion/removal path.

In some embodiments of the present disclosure, the insertion/removal path may be disposed on a plane such as a coronal plane. The insertion/removal path may include a continuous curve. The insertion/removal path may include a spline, a polynomial, an exponential, or a logarithmic function line.

In some embodiments of the present disclosure, the generating at 630 the three-dimensional data representing the initial implant may include program code for obtaining, by the one or more processors, data representing a proximal end of the initial implant, and data representing a distal end of the initial implant. The generating at 640 data representing an insertion/removal path may include program code for obtaining, via the processor, data representing a femoral neck axis of the femur, and a femoral shaft axis of the femur.

In some embodiments of the present disclosure, the generating at 630 data representing the three-dimensional data representing the initial implant may include program code for obtaining, by the one or more processors, data representing a proximal end of the initial implant, and data representing a distal end of the initial implant, and the generating at 630 data representing the insertion/removal path may include program code for obtaining, by the one or more processors, data representing a femoral neck axis of the femur, and a femoral shaft axis of the femur, and the insertion path at the proximal end of the initial implant is axially aligned along the femoral neck axis, and the insertion path at the distal end of the initial implant is axially aligned with the femoral shaft axis of the femur.

An embodiment for solving the problem of stability and insertability of the femoral stem or femoral sleeve component in a total hip replacement, for example, may be through a computer implemented method utilizing programming code in a recursive process, whereby an implant is designed that maximizes cortical contact from a proximal member along the femoral neck axis to a distal location along the long axis of the femur. Rather than calculating an insertion path, the present technique is directed to program code that begins with an initial implant representation. FIGS. 14-17 diagrammatically illustrate a computerized process, for example, implemented, by programming code for use in forming a patient specific femoral stem of a femoral component for total hip replacement, according to an embodiment of the present disclosure.

Figure 14:
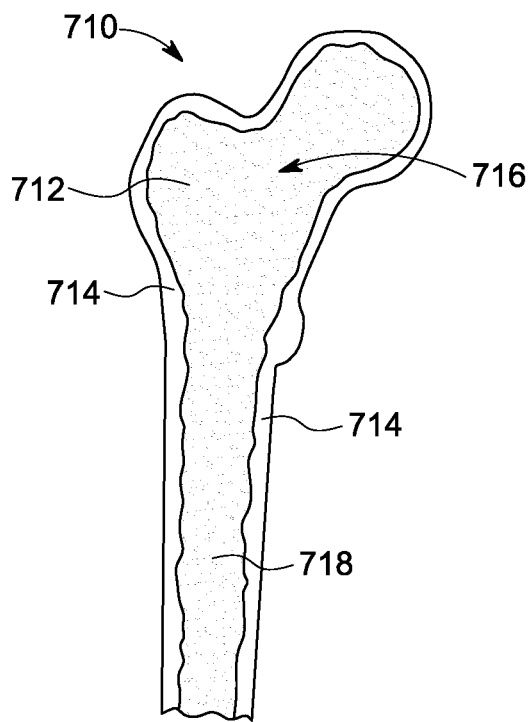
FIGS. 14-17 are cross-sectional views diagrammatically illustrating a computerized process for use in forming a patient specific femoral stem of a femoral component for total hip replacement, according to an embodiment of the present disclosure.

For example, FIG. 14 illustrates a proximal portion of a patient's femur 710 having centralized cancellous bone 712 and peripheral cortical bone 714. For example, data representing the proximal portion of the patient's femur 710 may include three-dimensional data obtained by, for example, a Computed Tomography (CT) scan, a Computerized Axial Tomography (CAT) scan, a Magnetic Resonance Imaging (MRI) scan, or other suitable two-dimensional imaging or three-dimensional imaging or processing. A surgeon may input a proximal extreme location 716 and a distal extreme location 718 of the desired patient customized femoral stem implant for the femur 710. Alternative, the proximal extreme location 716 and the distal extreme location 718 may be determined and generated by program code.

Figure 15:
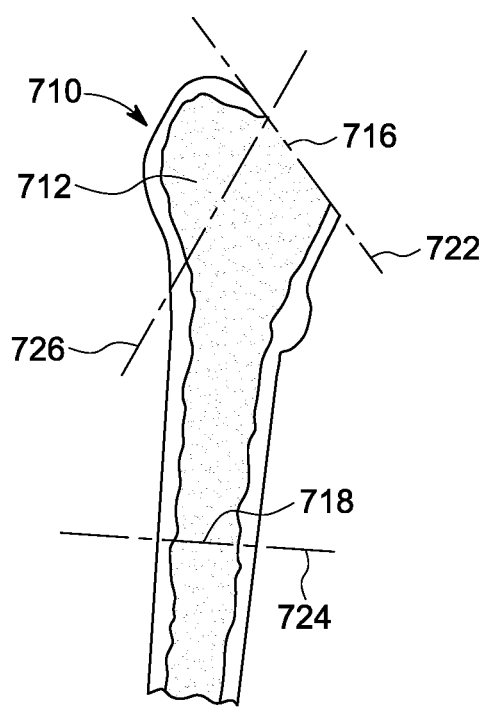

In this approach, as shown in FIG. 15, a plane 722 having an orientation relative to the proximal femur may be generated at the proximal extreme location 716 and a plane 724 having an orientation relative to the femur shaft may be generated at the distal extreme location 718. In some embodiments, the planes may be normal to a femoral neck axis (not show in FIG. 15) and normal to a femoral shaft axis (not shown in FIG. 15). A further plane 726 may be generated and orientated through the centralized cancellous bone 712 to define a portion of a boundary for forming the patient specific femoral stem. In other embodiments, a plane may be used that lies in a sagittal plane of the patient and may be used to set a lateral boundary for the initial surface generated at proximal extreme location 716. Alternatively, a surgeon may input planes 722, 724, and 726, and the orientations thereof. In some embodiments, a resection plane, such as plane 722 may be provided, e.g., by input by a surgeon, or based on or utilizing predetermined data. For example, the resection plane or plane 722 may be determined as disclosed in U.S. patent application Ser. No. 16/153,334, entitled, "Apparatus, Method and System for Providing Customizable Bone Implants", the entire subject matter of which is incorporated herein by reference.

Figure 16:
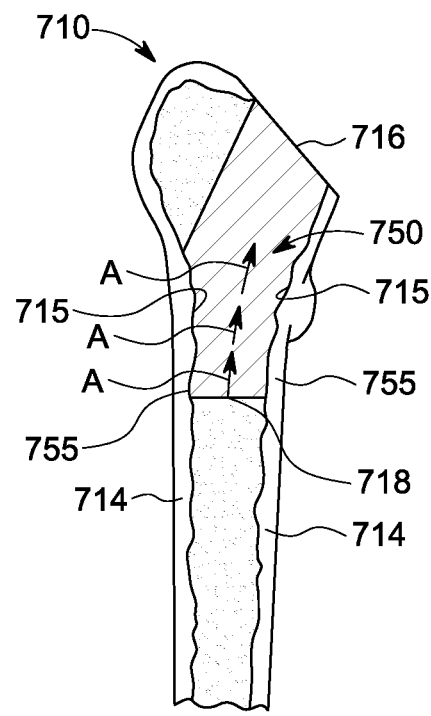

With reference to FIG. 16, an initial implant or femoral stem 750 is constructed. The initial implant 750 is generated between the proximal extreme location 716 and the distal extreme location 718. The initial implant 750 has an outer surface that corresponds to an inner surface 715 of the cortical bone 714, and along the boundary or plane 726 (FIG. 15).

Figure 17:
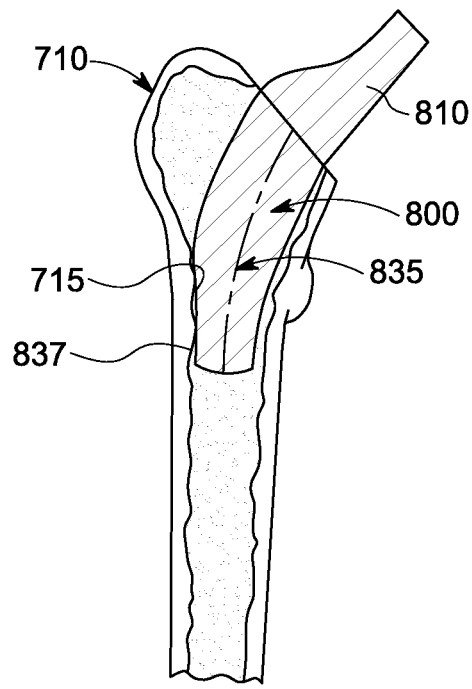

The computerized process includes the initial implant 750 having an outer surface within a conforming cavity defined by the cortical bone 715 of the femur 710 and boundary or plane 726 and calculates or generates an extraction path for the initial inserted femoral stem 750. The initial implant 750 may be free to move with six-degrees of freedom in a series of small step movements, for example, as indicated by arrows A, biased to a rigid transformation that minimizes the collision of the most points along the outer surface 755 of the initial implant 750 with the inner surface 715 of the cortical bone 714. The algorithm or program code identifies all of the points causing interferences for that incremental step and removes them from the initial implant 750, resulting in a resultant femoral stem 800 as shown in FIG. 17. The algorithm or program code also records the rigid transformation for each incremental step such that such transformations can be re-integrated into an insertion trajectory 835. The process may be repeated to generate an optimized resultant patient specific femoral stem 800 having a shape that maximizes cortical contact when installed in the patient along the insertion trajectory 835. A neck component 810 may be generated and attachable or integral with femoral stem 800. In some embodiments, the resultant femoral stem 800 includes asymmetric cross-sections. In some embodiments, portions, such as portion 837, of the outer surface of outer surface of the resultant femoral stem 800, may match the corresponding contour and shape of the patient's inner cortical bone surface 715 of the femur 10.

An embodiment for solving the problem of stability and insertability of a femoral sleeve component in a total hip replacement, for example, may be through a computer implemented method utilizing programming code in a recursive process, whereby an implant is designed that maximizes cortical contact from a proximal member along the long axis of the femur. Rather than calculating an insertion path, the present technique is directed to program code that begins with an initial implant representation. FIGS. 18-21 diagrammatically illustrate a computerized process, for example, implemented, by programming code for use in forming a patient specific femoral sleeve of a femoral component for total hip replacement, according to an embodiment of the present disclosure.

Figure 18:
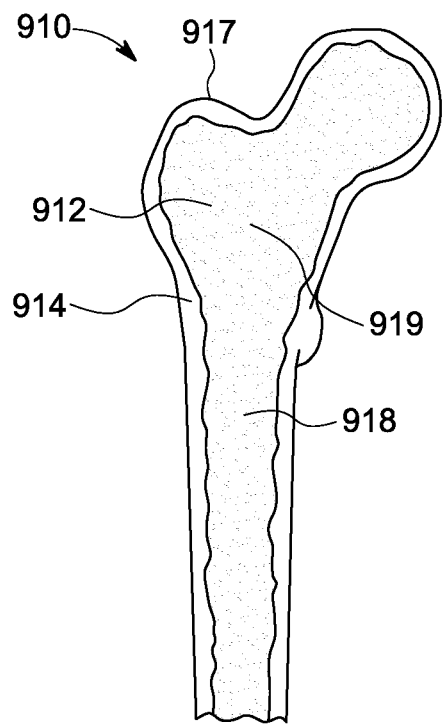
FIGS. 18-21 are cross-sectional views diagrammatically illustrating a computerized process for use in forming a patient specific femoral sleeve of a femoral component for total hip replacement, according to an embodiment of the present disclosure.

For example, FIG. 18 illustrates a proximal portion of a patient's femur 910 having centralized cancellous bone 912 and peripheral cortical bone 914. For example, data representing the proximal portion of the patient's femur 910 may include three-dimensional data obtained by, for example, a Computed Tomography (CT) scan, a Computerized Axial Tomography (CAT) scan, a Magnetic Resonance Imaging (MRI) scan, or other suitable two-dimensional imaging or three-dimensional imaging or processing. A surgeon may input a proximal extreme location 917, a distal extreme location 918, and a mid-location 919 of the desired patient customized femoral sleeve implant for the femur 910. Alternative, the proximal extreme location 917, the distal extreme location 918, and the mid location 919 may be determined and generated by program code. Other features may be used of the patient's femur and/or used in conjunction with data representing the standard femoral stem 470 (FIG. 12) and the femoral neck implant 410 (FIG. 12) (e.g., superimposed) and may be determined and generated by program code.

Figure 19:
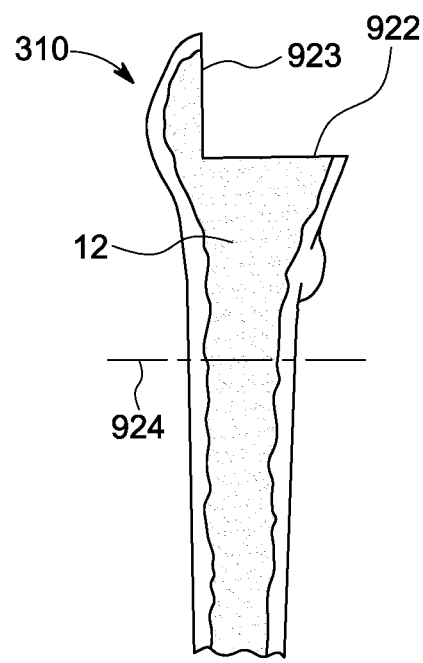

In this approach, as shown in FIG. 19, a first plane 922 having an orientation relative to the proximal femur may be generated at the mid location 919 (FIG. 18), a second plane 923 having an orientation relative to the proximal femur may be generated at the mid location 919 (FIG. 18), and a third plane 924 having an orientation relative to the proximal femur may be generated at the distal location 924 (FIG. 18). The first plane and the second plane may correspond to the resection planes.

In some embodiments, the first and second planes may be normal or perpendicular to each other, and the first plane and the third plane may normal or perpendicular to a femoral shaft axis. Alternatively, a surgeon may input planes 922, 923, and 924, and the orientations thereof. In some embodiments, resection planes, such as first plane 922 and second plane 923 may be provided, e.g., by input by a surgeon, or based on or utilizing predetermined data.

Figure 20:
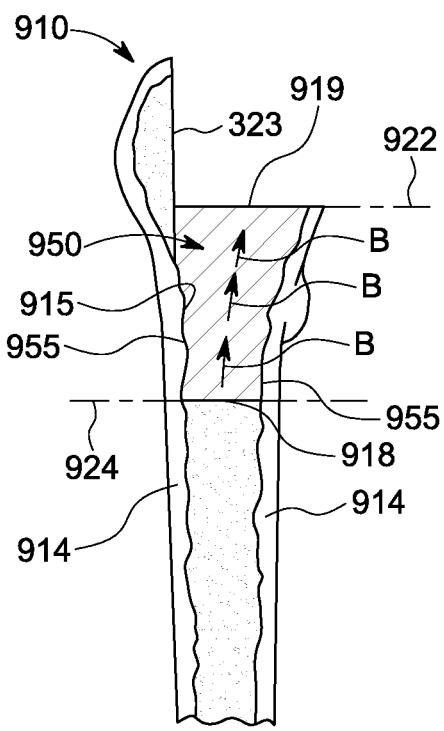

As shown in FIG. 20, an initial implant or femoral sleeve 950 is constructed. The initial implant 950 is generated between the mid location 919 and the distal extreme location 918. The initial implant 950 may have an outer surface that corresponds to an inner surface 915 of the cortical bone 914, the first plane 922, and the third plane 924.

Figure 21:
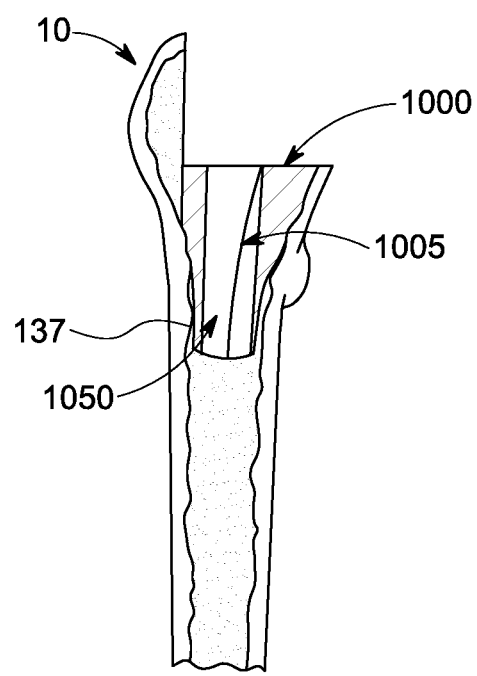

The computerized process includes the initial implant 950 having an outer surface within a conforming cavity defined by the cortical bone 915 of the femur 910 and boundary or planes 922 and 924 and calculates or generates an extraction path for the initial inserted femoral stem 950. The initial implant 950 may be free to move with six-degrees of freedom in a series of small step movements, for example, as indicated by arrows B, biased to a rigid transformation that minimizes the collision of the most points along the outer surface 955 of the initial implant 950 with the inner surface 915 of the cortical bone 914. The algorithm or program code identifies all of the points causing interferences for that incremental step and removes them from the initial implant 950, resulting in a resultant femoral sleeve 1000 as shown in FIG. 21. The algorithm or program code also records the rigid transformation for each incremental step such that such transformations can be re-integrated into an insertion trajectory 1005. The process may be repeated to generate an optimized resultant patient specific femoral sleeve 1000 having a shape that maximizes cortical contact when installed in the patient along the insertion trajectory 1005. A passageway 1050 may be generated for receiving a standard femoral stem and neck, such as femoral stem 470 (FIG. 12) and neck 410 (FIG. 12).

Figure 22:
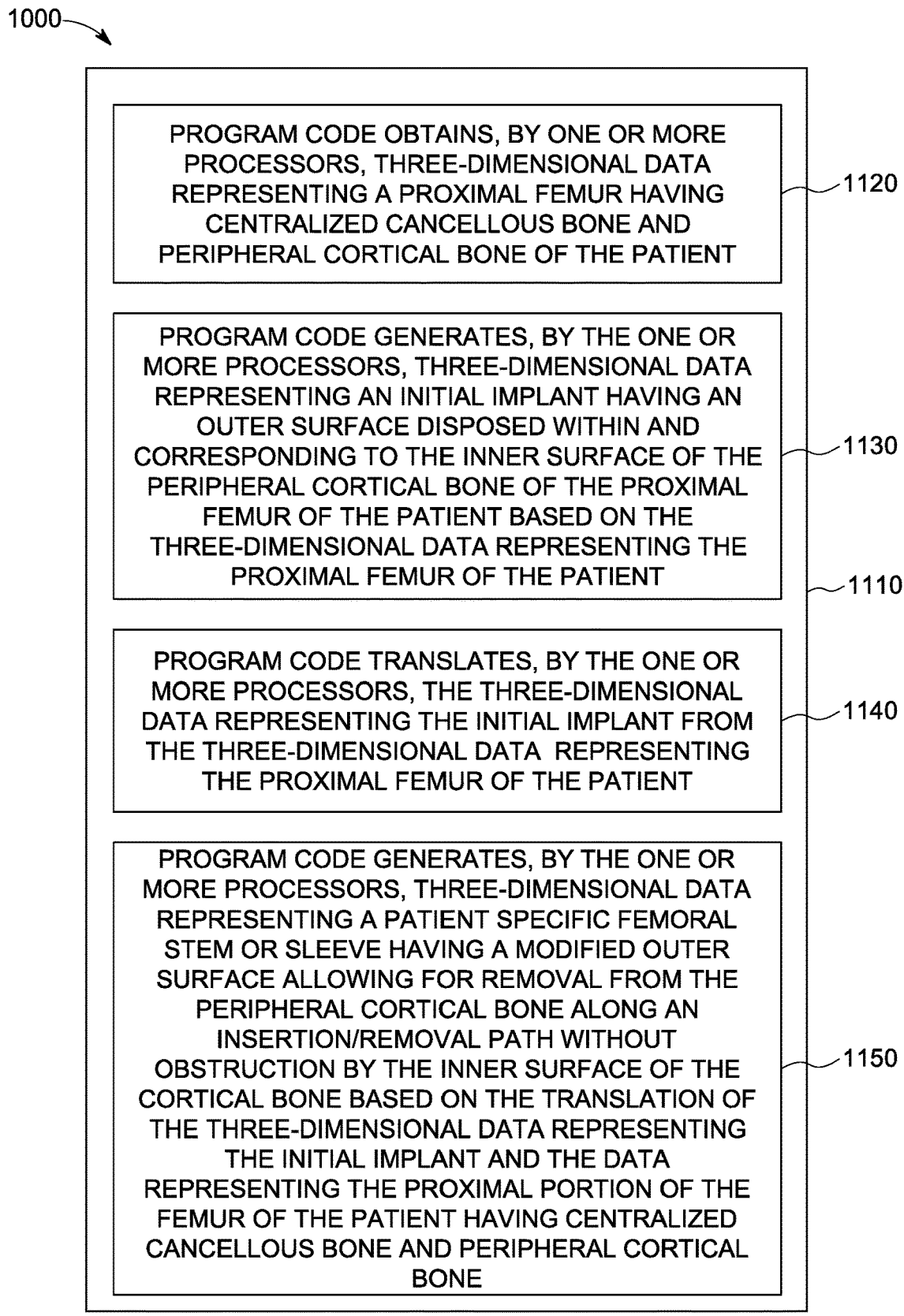
FIG. 22 is a workflow that depicts certain aspects of some embodiments of the present disclosure.

FIG. 22 illustrates a workflow 1100 that depicts certain aspects of some embodiments of the present disclosure for use in forming a patient specific femoral stem or femoral sleeve of a femoral component for total hip replacement. In some embodiments of the present disclosure, a program code 1110 (also referred to as one or more programs) executed by a processing circuit or hardware, obtains at 1120, by one or more processors, three-dimensional data representing a proximal femur of the patient having centralized cancellous bone and peripheral cortical bone. At 1130, three-dimensional data representing an initial implant having an outer surface disposed within and corresponding to the inner surface of the peripheral cortical bone of the proximal femur of the patient is generated, by the one or more processors, based on the three-dimensional data representing a proximal femur of the patient. At 1140, the three-dimensional data representing the initial implant is translated, by the one or more processors, from the three-dimensional data representing the proximal femur of the patient. At 1150, three-dimensional data representing a patient specific femoral stem or sleeve having a modified outer surface allowing for removal from the peripheral cortical bone along an insertion/removal path without obstruction by the inner surface of the cortical bone is generated, by the one or more processors, based on the translation of the three-dimensional data representing the initial implant and the data representing the proximal portion of the femur of the patient having centralized cancellous bone and peripheral cortical bone.

In some embodiments of the present disclosure, the workflow 1100 may further include program code for fabricating, by the one or more processors, the femoral stem or sleeve based on the three-dimensional data representing the patient specific femur.

In some embodiments of the present disclosure, the translating 1140 may include program code for translating, by the one or more processors, the three-dimensional data representing the initial implant a plurality of incremental translations from the three-dimensional data representing the proximal femur of the patient, and wherein each of the plurality of incremental translation includes a plurality of different translations, and program code for selecting, by the one or more processors, one of the different translations based on the different translation requiring the least modification of the initial implant.

In some embodiments of the present disclosure, the translating 1140 may include program code for translating, by the one or more processors, the three-dimensional data representing the initial implant in a plurality of incremental translations from the three-dimensional data representing the proximal femur of the patient, and the generating may include program code for generating, by the one or more processors, the three-dimensional data representing the patient specific femoral stem or sleeve based on the translating the three-dimensional data representing the initial implant in the plurality of incremental translations.

In some embodiments of the present disclosure, the translating 1140 may include program code for translating, by the one or more processors, the three-dimensional data representing the initial implant in a plurality of incremental straight line translations from the three-dimensional data representing the proximal femur of the patient, and the generating may include program code for generating, by the one or more processors, the three-dimensional data representing the patient specific femoral stem or sleeve based on the translating the three-dimensional data representing the initial implant in the plurality of incremental straight line translations. In addition, the translating 1140 may include program code for translating, by the one or more processors, the three-dimensional data representing the initial implant along a coronal plane from the three-dimensional data representing the proximal femur of the patient, and the generating may include program code for generating, by the one or more processors, the three-dimensional data representing the patient specific femoral stem or sleeve based on the translating the three-dimensional data representing the initial implant along the coronal plane.

In some embodiments of the present disclosure, the translating 1140 may include program code for translating and rotating, by the one or more processors, the three-dimensional data representing the initial implant from the three-dimensional data representing the proximal femur of the patient, and the generating may include program code for generating, via the processor, the three-dimensional data representing the patient specific femoral stem or sleeve based on the translating the three-dimensional data representing the initial implant in the coronal plane.

Figure 23:
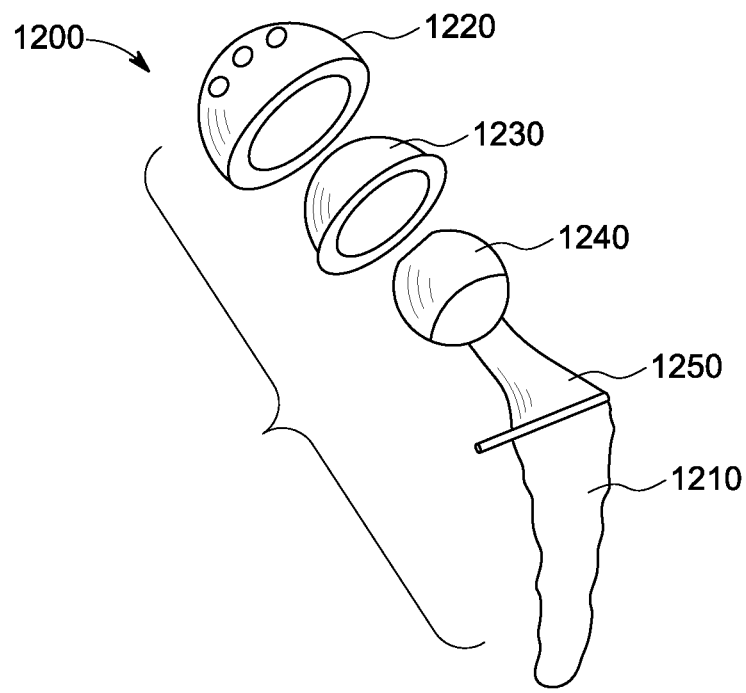
FIG. 23 is a perspective view of a hip arthroplasty system, according to an embodiment of the present disclosure.

FIG. 23 illustrates a hip arthroplasty system 1200 having a patient specific femoral stem component 1210, according to an embodiment of the present disclosure. For example, a patient specific femoral stem component 1210 may be designed and fabricated as described above. In this illustrated embodiment, arthroplasty system 1200 may include an acetabular component 1220, a bearing liner 1230, a femoral head 1240, a femoral neck 1250, and the patient specific femoral stem component 1210.

Figure 24:
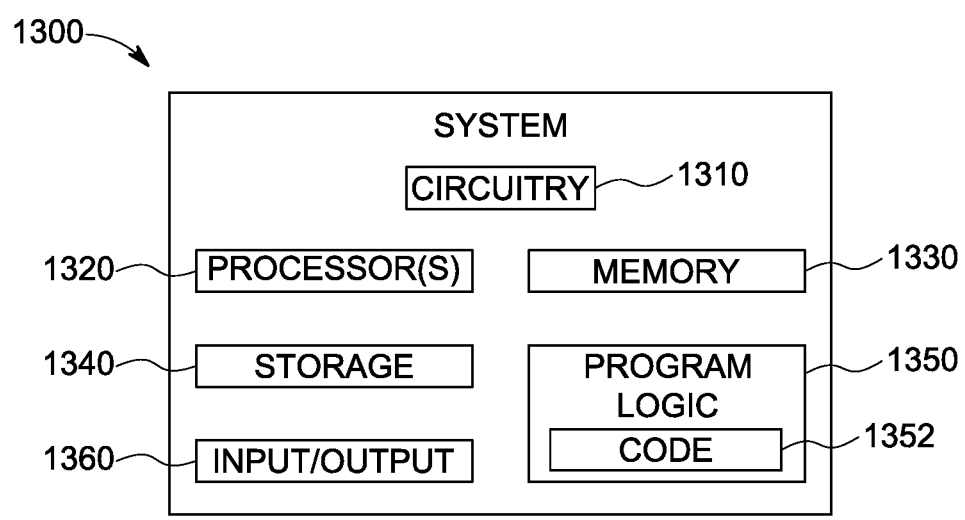
FIG. 24 depicts a computer system configured to perform an aspect of an embodiment of the present disclosure.

FIG. 24 illustrates a block diagram of a computer system 1300, which is part of the technical architecture of the embodiments of the present disclosure. System 1300 may include a circuitry 1310 that may in certain embodiments include a microprocessor 1320. The system 1300 may also include a memory 1330 (e.g., a volatile memory device), and storage 1340. The system 1300 may include a program logic 1350 including code 1352 that may be loaded into or stored in the memory 1330, the storage 1340, and/or circuitry 1310, and executed by the microprocessor 1320 and/or circuitry 1310. The various components may be operably coupled directly or indirectly via a system bus or may be coupled directly or indirectly to other data processing systems and components. The program logic 1350 may include the program code discussed above in this disclosure for use in forming a patient specific femoral stem or femoral sleeve of a femoral component for total hip replacement.

As will be appreciated by one skilled in the art, aspects of the technique may be embodied as a system, method, or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system".

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. Each block in the flowchart or block diagrams may represent a module, segment, or portion of code, which includes one or more executable instructions for implementing the specified logical function(s).

These computer program instructions, also referred to as software and/or program code, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. For example, in a particular arrangement, a desktop or workstation computer may be employed using a commercially available operating system, e.g. Windows®, OSX®, UNIX or Linux based implementation.

The computer readable storage medium 1340 may be, for example, but not limited to, an electronic, magnetic, optical, electromagnetic, infrared or semiconductor system, apparatus, or device, or any suitable combination of the foregoing. The storage 1340 may include an internal storage device, an attached storage device and/or a network accessible storage device. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program code for carrying out operations for aspects of the present technique may be written in any combination of one or more programming languages, including an object oriented programming language, such as Java, Smalltalk, C++ or the like, and conventional procedural programming languages, such as the "C" programming language, PHP, ASP, assembler or similar programming languages, as well as functional programming languages and languages for technical computing. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Furthermore, more than one computer can be used for implementing the program code, including, but not limited to, one or more resources in a cloud computing environment.

Input/output or I/O devices 1360 (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Data relating to a patient, e.g., the patient's pelvis and hip, may be created by, or accessed from, a medical sensor device. For example, previous medical scans of an extremity, such as those obtained from a computerized axial tomography (CAT or CT) or magnetic resonance imaging (MRI) scan may be stored in a medical record storage apparatus, in storage 1340, or accessed by system 1300. Such patient data may include other data for a given patient (e.g. bone density, type, length, medical conditions etc.). By way of a non-limiting example, the patient data may include a scan data set containing a series of two-dimensional images obtained from the scanning device (e.g. CT scan slices). As such, the scan data set is a 3D dimensional representation of the scan data.

From the present disclosure, it will be appreciated that the technique of the present disclosure for design of patient specific femoral stem or femoral sleeve implants overcome the problems of conventional femoral stem or femoral sleeve implants. The technique of the present disclosure may include program algorithms and code to pre-operatively simulate surgical insertion of the generic implants or customized patient specific femoral stem or femoral sleeve implants. The present disclosure overcomes the problems with population-based design, which require both obtaining or access to large segmented data pools of CT scans, which is extremely costly, and designing standardized implants, which is time consuming, costly, and labor intensive. Proper classification and treatment of the population classifications can also increase cost, for example, if higher degrees of refinement are sought on the population classifications, which necessitate both increased analysis and number of discrete implants that need to be designed.

The technique of the present disclosure allows determining or optimizing a minimum size for the femoral stem or femoral sleeve implants, which overcomes generic implants that tend to be longer and thinner and result in more trauma to the femur upon insertion.

From the present description, it will be appreciated that the technique of the present disclosure allows for pre-operative insertability analysis and helps facilitate the design of customize implants by simulating insertability. The present disclosure may be useful for simulating the insertion of both generic and custom implants as well as for the design of both generic and custom implants. The present disclosure may be used with surgical procedures that employ a surgical robot. The present disclosure may be useful for pre-operative simulations of a surgical procedure.

From the present description, the technique of the present disclosure includes a computer implemented methods for simulating insertion of generic and custom orthopedic hip implants. Computer implemented methods include simulating the insertion of generic and custom implants and include simulating the removal of an inserted implant and developing an implant around an optimized insertion trajectory.

As may be recognized by those of ordinary skill in the art based on the teachings herein, numerous changes and modifications may be made to the above-described and other embodiments of the present disclosure without departing from the scope of the disclosure. The implants, screws, and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The present disclosure has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the present disclosure be construed as including all such modifications and alterations.

The invention claimed is:

1. A computer implemented method for use in forming a patient specific femoral stem or sleeve of a femoral component for total hip replacement, the computerized method comprising:
   obtaining, by one or more processors, three-dimensional data representing a proximal portion of a femur of the patient having centralized cancellous bone and peripheral cortical bone;
   generating, by the one or more processors, three-dimensional data representing an initial implant having an outer surface corresponding to the inner surface of the peripheral cortical bone of the proximal femur of the patient based on the three-dimensional data representing the proximal portion of the femur of the patient;
   generating, by the one or more processors, data representing an insertion/removal path through the centralized cancellous bone based on the three-dimensional data representing the proximal portion of the femur of the patient;
   generating, by the one or more processors, three-dimensional data representing the patient specific femoral stem or sleeve having a modified outer surface allowing for removal and insertion adjacent to the peripheral cortical bone along the insertion/removal path without obstruction by the inner surface of the cortical bone based on the three-dimensional data representing the proximal portion of the femur of the patient and the data representing the insertion/removal path;
   wherein the generating the three-dimensional data representing the patient specific femoral stem or sleeve comprises:
      translating, by the one or more processors, the three-dimensional data representing the initial implant along the data representing the insertion/removal path; and
      modifying, by the one or more processors, the three-dimensional data representing the initial implant based on the translation of the initial implant along the data representing insertion/removal path and the three-dimensional data representing the proximal portion of the femur of the patient; and
   wherein:
   the translating comprises translating, by the one or more processors, the three-dimensional data representing the initial implant without rotation along the insertion/removal path; and/or
   the translating comprises translating, by the one or more processors, the three-dimensional data representing the initial implant along the insertion/removal path along a plane.

2. The computer implemented method of claim 1, further comprising fabricating, by the one or more processors, the patient specific femoral stem or sleeve based on the three-dimensional data representing the patient specific femoral stem or sleeve.

3. The computer implemented method of claim 1, wherein:
   the translating comprises translating, by the one or more processors, the three-dimensional data representing the initial implant without rotation along the insertion/removal path and/or; and
   the translating comprises translating, by the one or more processors, the three-dimensional data representing the initial implant along the insertion/removal path along a plane.

4. The computer implemented method of claim 1, wherein the translating comprises translating, by the one or more processors, the three-dimensional data representing the initial implant along the insertion/removal path concentric with at least a portion of a femoral shaft axis and/or at least a portion of a femoral neck axis.

5. The computer implemented method of claim 1, wherein the generating the three-dimensional data representing the initial implant comprises:
   obtaining, by the one or more processors, data representing a proximal end of the initial implant, and data representing a distal end of the initial implant; and/or
   generating, by the one or more processors, data representing a proximal end of the initial implant, and data representing a distal end of the initial implant.

6. The computer implemented method of claim 1, further comprising:
   generating, by the one or more processors, data representing at least one resection plane through the proximal portion of the femur of the patient.

7. The computer implemented method of claim 1, wherein the insertion/removal path lies on a plane.

8. The computer implemented method of claim 1, wherein the insertion/removal path lies on a coronal plane.

9. The computer implemented method of claim 1, wherein the insertion/removal path comprises a continuous curve.

10. The computer implemented method of claim 1, wherein the insertion/removal path comprises a spline, a polynomial, an exponential, or a logarithmic function line.

11. The computer implemented method of claim 1, wherein the insertion/removal path comprises a straight line.

12. The computer implemented method of claim 1, wherein the insertion/removal path comprises a straight line coaxial with a femoral shaft axis.

13. A system comprising:
a memory;
one or more processors in communication with the memory; and
program instructions executable by the one or more processors via the memory to perform the method of claim 1.

14. A computer program product comprising:
a computer readable storage medium readably by one or more processing circuit and storing instructions for execution by one or more processors for performing the method of claim 1 for use in forming a patient specific femoral stem or sleeve of a femoral component for total hip replacement.

15. A computer implemented method for use in forming a patient specific femoral stem or sleeve of a femoral component for total hip replacement, the computerized method comprising:
obtaining, by one or more processors, three-dimensional data representing a proximal portion of a femur having centralized cancellous bone and peripheral cortical bone of the patient;
generating, by the one or more processors, three-dimensional data representing an initial implant having an outer surface corresponding to the inner surface of the peripheral cortical bone of the proximal portion of the femur of the patient based on the three-dimensional data representing the proximal portion of the femur of the patient;
translating, by the one or more processors, the three-dimensional data representing the initial implant from the three-dimensional data representing the proximal portion of the femur of the patient;
generating, by the one or more processors, three-dimensional data representing a patient specific femoral stem or sleeve having a modified outer surface allowing for removal from the peripheral cortical bone along an insertion/removal path without obstruction by the inner surface of the cortical bone based on the translation of the three-dimensional data representing the initial implant and the proximal portion of the femur having centralized cancellous bone and peripheral cortical bone of the patient; and
wherein the translating comprises translating, by the one or more processors, the three-dimensional data representing the initial implant by a plurality of incremental translations from the three-dimensional data representing the proximal femur of the patient; and
the generating comprises generating, by the one or more processors, the three-dimensional data representing the patient specific femoral stem or sleeve based on the plurality of incremental translations.

16. The computer implemented method of claim 15, further comprising fabricating, by the one or more processors, the patient specific femoral stem or sleeve based on the three-dimensional data representing the patient specific femoral stem or sleeve.

17. The computer implemented method of claim 15, wherein:

the plurality of incremental translations comprises a series of different plurality of incremental translations from the three-dimensional data representing the proximal femur of the patient;
the translating comprises translating, by the one or more processors, the three-dimensional data representing the initial implant by the series of different plurality of incremental translations from the three-dimensional data representing the proximal femur of the patient; and
the generating comprises selecting, by the one or more processors, the three- dimensional data representing the patient specific femoral stem or sleeve based one of the series of different plurality of incremental translations requiring a reduced modification of the initial implant.

18. The computer implemented method of claim 15, wherein:
the plurality of incremental translations comprises a plurality of incremental straight line translations from the three-dimensional data representing the proximal femur of the patient;
the translating comprises translating, by the one or more processors, the three-dimensional data representing the initial implant in the plurality of incremental straight line translations from the three-dimensional data representing the proximal femur of the patient; and
the generating comprises generating, by the one or more processors, the three-dimensional data representing the patient specific femoral stem or sleeve based on the translating the three-dimensional data representing the initial implant in the plurality of incremental straight line translations.

19. A system comprising:
a memory;
one or more processors in communication with the memory; and
program instructions executable by the one or more processors via the memory to perform the method of claim 15.

20. A computer program product comprising:
a computer readable storage medium readably by one or more processing circuit and storing instructions for execution by one or more processors for performing the method of claim 15 for use in forming a patient specific femoral stem or sleeve of a femoral component for total hip replacement.

21. A computer implemented method for use in forming a patient specific femoral stem or sleeve of a femoral component for total hip replacement, the computerized method comprising:
obtaining, by one or more processors, three-dimensional data representing a proximal portion of a femur of the patient having centralized cancellous bone and peripheral cortical bone;
generating, by the one or more processors, three-dimensional data representing an initial implant having an outer surface corresponding to the inner surface of the peripheral cortical bone of the proximal femur of the patient based on the three-dimensional data representing the proximal portion of the femur of the patient;
generating, by the one or more processors, data representing an insertion/removal path through the centralized cancellous bone based on the three-dimensional data representing the proximal portion of the femur of the patient;
generating, by the one or more processors, three-dimensional data representing the patient specific femoral stem or sleeve having a modified outer surface allowing for removal and insertion adjacent to the peripheral cortical bone along the insertion/removal path without obstruction by the inner surface of the cortical bone based on the three-dimensional data representing the proximal portion of the femur of the patient and the data representing the insertion/removal path;

wherein the generating the three-dimensional data representing the patient specific femoral stem or sleeve comprises:

translating, by the one or more processors, the three-dimensional data representing the initial implant along the data representing the insertion/removal path; and modifying, by the one or more processors, the three-dimensional data representing the initial implant based on the translation of the initial implant along the data representing insertion/removal path and the three-dimensional data representing the proximal portion of the femur of the patient; and wherein:

the generating data representing the insertion/removal path comprises generating, by the one or more processors, data representing a plurality of different insertion/removal paths;

the translating comprises translating, by the one or more processors, the three-dimensional data representing the initial implant along the data representing the plurality of different insertion/removal paths; and the modifying comprises modifying, by the one or more processors, the three-dimensional data representing the initial implant based on the translation of the initial implant separately along the data representing each of the plurality of different insertion/removal paths and the three-dimensional data representing the proximal portion of the femur of the patient; and further comprising:

comparing, by the one or more processors, the plurality of modified patient specific femoral stems or sleeves and selecting, by the one or more processors, one of the plurality of modified patient specific femoral stems or sleeves based on the amount of the outer surface of the modified patient specific femoral stems or sleeves engagable with the inners surface of the cortical bone when the modified patient specific femoral stem or sleeve is installed in the proximal portion of the femur of the patient.

22. The computer implemented method of claim 21, further comprising fabricating, by the one or more processors, the patient specific femoral stem or sleeve based on the three-dimensional data representing the patient specific femoral stem or sleeve.

23. A computer implemented method for use in forming a patient specific femoral stem or sleeve of a femoral component for total hip replacement, the computerized method comprising:

obtaining, by one or more processors, three-dimensional data representing a proximal portion of a femur of the patient having centralized cancellous bone and peripheral cortical bone;

generating, by the one or more processors, three-dimensional data representing an initial implant having an outer surface corresponding to the inner surface of the peripheral cortical bone of the proximal femur of the patient based on the three-dimensional data representing the proximal portion of the femur of the patient;

generating, by the one or more processors, data representing an insertion/removal path through the centralized cancellous bone based on the three-dimensional data representing the proximal portion of the femur of the patient;

generating, by the one or more processors, three-dimensional data representing the patient specific femoral stem or sleeve having a modified outer surface allowing for removal and insertion adjacent to the peripheral cortical bone along the insertion/removal path without obstruction by the inner surface of the cortical bone based on the three-dimensional data representing the proximal portion of the femur of the patient and the data representing the insertion/removal path; and wherein the generating data representing an insertion/removal path comprises:

obtaining, by the one or more processors, data representing a femoral shaft axis of the femur and/or a femoral neck axis of the femur, and wherein the insertion/removal path is based on the femoral shaft axis and/or the femoral neck axis; and/or generating, by the one or more processors, data representing a femoral shaft axis of the femur, and a femoral neck axis of the femur, and wherein the insertion/removal path is based on a femoral shaft axis and/or a femoral neck axis.

24. The computer implemented method of claim 23, further comprising fabricating, by the one or more processors, the patient specific femoral stem or sleeve based on the three-dimensional data representing the patient specific femoral stem or sleeve.

25. A computer implemented method for use in forming a patient specific femoral stem or sleeve of a femoral component for total hip replacement, the computerized method comprising:

obtaining, by one or more processors, three-dimensional data representing a proximal portion of a femur of the patient having centralized cancellous bone and peripheral cortical bone;

generating, by the one or more processors, three-dimensional data representing an initial implant having an outer surface corresponding to the inner surface of the peripheral cortical bone of the proximal femur of the patient based on the three-dimensional data representing the proximal portion of the femur of the patient;

generating, by the one or more processors, data representing an insertion/removal path through the centralized cancellous bone based on the three-dimensional data representing the proximal portion of the femur of the patient;

generating, by the one or more processors, three-dimensional data representing the patient specific femoral stem or sleeve having a modified outer surface allowing for removal and insertion adjacent to the peripheral cortical bone along the insertion/removal path without obstruction by the inner surface of the cortical bone based on the three-dimensional data representing the proximal portion of the femur of the patient and the data representing the insertion/removal path; and wherein:

the generating the three-dimensional data representing the initial implant comprises:

obtaining, by the one or more processors, data representing a proximal end of the initial implant and data representing a distal end of the initial implant;

the generating data representing the insertion/removal path comprises:

obtaining, by the one or more processors, data representing a femoral shaft axis of the proximal portion of the femur of the patient, and a femoral neck axis of the proximal portion of the femur of the patient; and wherein the insertion/removal path at the proximal end of the initial implant is coaxial with the femoral neck axis of the proximal portion of the femur of the patient, and the insertion/removal path at the distal end of the initial implant is coaxial with the femoral shaft axis of the proximal portion of the femur of the patient.

26. The computer implemented method of claim 25, further comprising fabricating, by the one or more processors, the patient specific femoral stem or sleeve based on the three-dimensional data representing the patient specific femoral stem or sleeve.

27. A computer implemented method for use in forming a patient specific femoral stem or sleeve of a femoral component for total hip replacement, the computerized method comprising:

obtaining, by one or more processors, three-dimensional data representing a proximal portion of a femur having centralized cancellous bone and peripheral cortical bone of the patient;

generating, by the one or more processors, three-dimensional data representing an initial implant having an outer surface corresponding to the inner surface of the peripheral cortical bone of the proximal portion of the femur of the patient based on the three-dimensional data representing the proximal portion of the femur of the patient;

translating, by the one or more processors, the three-dimensional data representing the initial implant from the three-dimensional data representing the proximal portion of the femur of the patient;

generating, by the one or more processors, three-dimensional data representing a patient specific femoral stem or sleeve having a modified outer surface allowing for removal from the peripheral cortical bone along an insertion/removal path without obstruction by the inner surface of the cortical bone based on the translation of the three-dimensional data representing the initial implant and the proximal portion of the femur having centralized cancellous bone and peripheral cortical bone of the patient; and wherein:

the translating comprises translating, by the one or more processors, the three-dimensional data representing the initial implant along a coronal plane from the three-dimensional data representing the proximal portion of femur of the patient; and the generating comprises generating, by the one or more processors, the three-dimensional data representing the patient specific femoral stem or sleeve based on the translating the three-dimensional data representing the initial implant along the coronal plane.

28. The computer implemented method of claim 27, further comprising fabricating, by the one or more processors, the patient specific femoral stem or sleeve based on the three-dimensional data representing the patient specific femoral stem or sleeve.

29. A computer implemented method for use in forming a patient specific femoral stem or sleeve of a femoral component for total hip replacement, the computerized method comprising:

obtaining, by one or more processors, three-dimensional data representing a proximal portion of a femur having centralized cancellous bone and peripheral cortical bone of the patient;

generating, by the one or more processors, three-dimensional data representing an initial implant having an outer surface corresponding to the inner surface of the peripheral cortical bone of the proximal portion of the femur of the patient based on the three-dimensional data representing the proximal portion of the femur of the patient;

translating, by the one or more processors, the three-dimensional data representing the initial implant from the three-dimensional data representing the proximal portion of the femur of the patient;

generating, by the one or more processors, three-dimensional data representing a patient specific femoral stem or sleeve having a modified outer surface allowing for removal from the peripheral cortical bone along an insertion/removal path without obstruction by the inner surface of the cortical bone based on the translation of the three-dimensional data representing the initial implant and the proximal portion of the femur having centralized cancellous bone and peripheral cortical bone of the patient; and wherein:

the translating comprises translating and rotating, by the one or more processors, the three-dimensional data representing the initial implant from the three-dimensional data representing the proximal femur of the patient; and the generating comprises generating, by the one or more processors, the three-dimensional data representing the patient specific femoral stem or sleeve based on the translating and rotating the three-dimensional data representing the initial implant the coronal plane.

30. The computer implemented method of claim 29, further comprising fabricating, by the one or more processors, the patient specific femoral stem or sleeve based on the three-dimensional data representing the patient specific femoral stem or sleeve.

* * * * *